United States Patent [19]

Lukàc et al.

[11] 4,323,711
[45] Apr. 6, 1982

[54] PROCESS FOR PRODUCING CYCLOHEXENES

[75] Inventors: Teodor Lukàc, Aesch; Erich Widmer, Münchenstein; Reinhard Zell, Rodersdorf, all of Switzerland

[73] Assignee: Hoffmann-La Roche Inc., Nutley, N.J.

[21] Appl. No.: 205,410

[22] Filed: Nov. 10, 1980

[30] Foreign Application Priority Data

Nov. 28, 1979 [CH] Switzerland ............... 10581/79

[51] Int. Cl.³ .................. C07C 45/62; C07C 45/00
[52] U.S. Cl. ................................................ 568/347
[58] Field of Search ............................. 568/347, 378

[56] References Cited

U.S. PATENT DOCUMENTS

| | | | |
|---|---|---|---|
| 3,624,105 | 11/1971 | Surmatis et al. | 568/347 |
| 4,098,827 | 7/1978 | Rosenberger | 568/347 |
| 4,157,345 | 6/1979 | Rosenberger | 568/347 |
| 4,204,073 | 5/1980 | Kienzle | 568/347 |

OTHER PUBLICATIONS

Akhrem et al., Chem. Abst., vol. 76, #45800w, (1972).
Morris et al., Chem. Abst., vol. 76, #112609f, (1972).
Fieser et al., "Reagents for Organic Synthesis, pp. 1276–1283, (1967), Wiley & Sons Inc.

*Primary Examiner*—Natalie Trousof
*Assistant Examiner*—James H. Reamer
*Attorney, Agent, or Firm*—Jon S. Saxe; George M. Gould; William H. Epstein

[57] ABSTRACT

A process for producing 3-(5-hydroxy-3-methyl-1,3-pentadienyl)-2,4,4-trimethyl-2-cyclohexen-1-one, an intermediate for canthaxanthin, by hydrogenation of 5-(2,6,6-trimethyl-3-oxo-cyclohexen-1-yl)-3-methyl-2-penten-4-yn-1-ol with zinc and a carboxylic acid.

5 Claims, No Drawings

PROCESS FOR PRODUCING CYCLOHEXENES

SUMMARY OF INVENTION

In accordance with this invention, a compound of the formula:

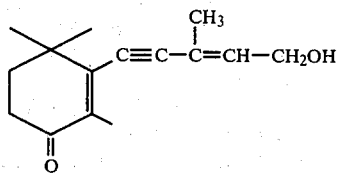

is hydrogenated by zinc and a carboxylic acid to produce a compound of the formula:

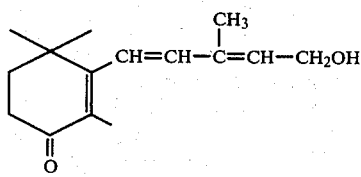

The compound of formula II can be converted to a phosphonium salt of the formula:

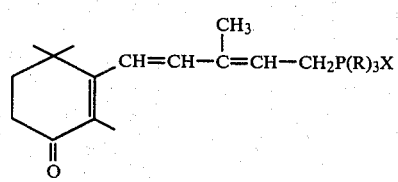

wherein R is phenyl and X is chlorine, bromine or iodine.

The compound of formula III is an intermediate for canthaxanthin.

DETAILED DESCRIPTION

The process in accordance with the invention is characterized in that a compound of the formula I

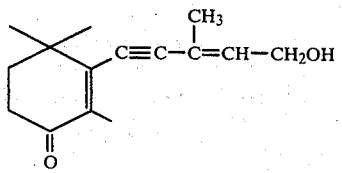

is hydrogenated by means of zinc and a carboxylic acid having from 1 to 3 carbon atoms, namely formic acid, acetic acid or propionic acid, and, if desired, the thereby obtained compound of the formula

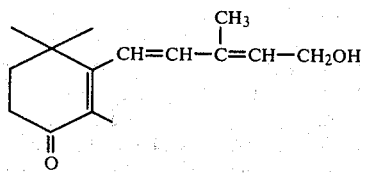

, after conversion into a phosphonium salt of the formula

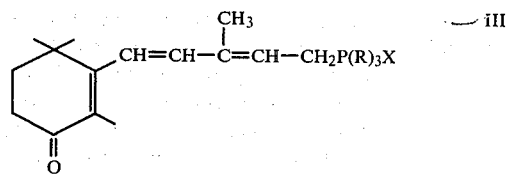

wherein R signifies phenyl and X signifies chlorine, bromine or iodine,
is converted into canthaxanthin.

The first step of this process, namely the partial hydrogenation of the compound of formula I to the compound of formula II is effected, as stated above, by means of zinc and a carboxylic acid having from 1 to 3 carbon atoms, namely with formic acid, acetic acid or propionic acid. An especially preferred embodiment consists in carrying out the hydrogenation with zinc and glacial acetic acid.

The hydrogenation reaction is generally carried out in a conventional inert organic solvent, for example, a chlorinated hydrocarbon, such as e.g. methylene chloride. While chlorinated hydrocarbons are preferred, any conventional inert organic solvent can be used in carrying out this hydrogenation reaction. On the other hand, the hydrogenation can be carried out in the absence of an inert organic solvent, in which case the acid itself then serves as the solvent.

There is preferably used an about 2% by weight solution of the starting material of formula I based on the weight of the mixture of solvent and acid. The ratio of solvent to acid, thus, for examples, the volume ratio of methylene chloride to glacial acetic acid, conveniently amounts to about 1:2 to 1:2.5 parts by volume.

For the purpose of completely carrying out the partial hydrogenation, zinc and acid should be used in at least stoichiometric amounts based on the starting material of formula I, but the combination of a zinc and acid excess is preferred.

The zinc is conveniently used in an amount of about 1 to about 3 gram atom, preferably about 1.5 gram per mol of starting material of formula I.

The reaction temperature chosen for the hydrogenation can lie within a wide temperature range, for example from about $-20°$ C. to about room temperature. In carrying out the hydrogenation reaction, temperatures of about $0°$ C. is preferred.

The thus-obtained compound of formula II can now be converted into a phosphonium salt of formula III and thereupon into canthaxanthin.

For the purpose of conversion of the compound of formula II into a phosphonium salt of formula III, the compound of formula II is first halogenated in a conventional manner such as by treatment with a hydrogen halide (hydrogen chloride, hydrogen bromide or hydrogen iodide) in aqueous solution (e.g. 48%, 63% or 57% by weight). In carrying out this halogenation, any conventional method of halogenating a primary alcohol can be used to carry out this reaction. This halogenation can be carried out at temperatures between about $-10°$ C. and about $+10°$ C., preferably at about $0°$ C. As the solvent there is hereby used any conventional inert organic solvent suitable for such halogenations, for example a chlorinated hydrocarbon, such as e.g. methylene chloride or chloroform.

The thus-obtained halide is thereupon converted into a phosphonium salt of formula III by reacting with a triarylphosphine, especially triphenylphosphine, in a manner known per se, for example in ethyl acetate, preferably in an inert gas atmosphere and in the presence of an acid-binding agent, e.g. an alkylene oxide, such as 1,2-butylene oxide, conveniently at room temperature or at somewhat elevated temperature. In forming the phosphonium salt, any conventional method of converting a halide to a phosphonium salt by reaction with triphenylphosphine can be used.

For the purpose of the manufacture of canthaxanthin from the phosphonium salt of formula III, the latter is reacted with the dialdehyde, i.e. 2,7-dimethyl-octatriene-(2,4,6)-dial-(1,8), whereby one likewise conveniently works in a suitable solvent, for example in methylene chloride or chloroform, and in the presence of an acid-binding agent, for example of 1,2-butylene oxide or sodium methylate. Any conventional method of carrying out a Wittig-type reaction can be used in this reaction.

The present invention further relates to a process for the manufacture of the compound of formula I used as the starting material according to the process described above.

This process for the manufacture of the compound of formula I is characterized in that a compound of the formula

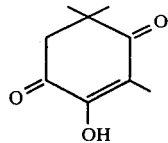

IV is reduced by means of zinc and a carboxylic acid with from up to 3 carbon atoms, namely with formic acid, acetic acid or propionic acid, to give a compound of the formula

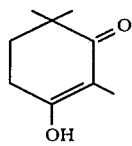

V

, the free hydroxy group of this compound is converted into a protected hydroxy group and the compound obtained is alkynylated with formation of a compound of formula I.

In the first step of this process, the reduction of the compound of formula IV is carried out in the same manner and utilizing the same conditions described in connection with the reduction of the compound of formula I. For instance, this reaction is carried out in an inert organic solvent, in especially a chlorinated hydrocarbon, e.g. ethylene chloride. On the other hand, this reaction can be carried out in the absence of an inert organic solvent. In this case, the acid itself functions as the solvent. The starting material is conveniently used in a concentration of about 5–15% by weight, for example about 10% by weight of the reaction medium. The zinc can be used, for example, in an amount of about 3 gram atom per mol of starting material. Convenient reaction temperatures are from about 45° C. to 80° C. with a temperature of about 75° C. being preferred.

An especially preferred embodiment consists in carrying out the reduction with zinc and formic acid.

The product obtained represents a tautomeric mixture of 3-hydroxy-2,6,6-trimethyl-2-cyclohexen-1-one (compound V) and 3-hydroxy-2,4,4-trimethyl-2-cyclohexen-1-one.

Thereupon, the free hydroxy group of the compound of formula V is protected by conventional means, for example by formation of a lower alkyl ether, e.g. the ethyl ether, and the thus-obtained ether is alkynylated with a protected 3-methyl-2-penten-4-yne, for example the acetone-methyl-(3-methyl-2-penten-4-ynyl)-acetal. This alkynylation is conveniently carried out in a solvent, for example tetrahydrofuran, with use of butyl lithium in a manner known per se, the primarily formed adduct being worked-up acid and being hydrolyzed to the compound of formula I.

The formulae contained herein are represented without regard to the cis/trans isomerism. Preferably, they are all-trans compounds. In the partial hydrogenation of formula I, the compound of formula II results predominantly in the 7-cis form. In the conversion of the compound of formula II into the phosphonium salt III, this results as usual in all-trans form under the reaction conditions described.

EXAMPLE 1

In a 2.5 liter sulfonation flask, provided with stirrer, thermometer, filled calcium chloride tube and an apparatus for inert gasification, 46.3 g of 5-(2,6,6-trimethyl-3-oxocyclohexen-1-yl)-3-methyl-2-trans-penten-4-yn-1-ol are dissolved in 1400 ml of methylene chloride and 300 ml of acetic acid while stirring and gassing with argon. Thereupon, the mixture is cooled to 0° C. with an alcohol/dry-ice cooling bath and 23.0 g of zinc dust are added and the mixture is further stirred at 0° C. for 3 hours under argon.

The still cold reaction mixture is filtered over a glass-internal suction filter and the residue is washed on the suction filter with 2 portions each of 100 ml, thus with a total of 200 ml, of methylene chloride.

Of four 3-liter separating funnels ($S_1$–$S_4$), $S_1$ is charged with 700 ml of ice-water, $S_2$ and $S_3$ are each charged with 1000 ml, thus with a total of 2000 ml, of saturated aqueous sodium bicarbonate solution and $S_4$ is charged with 500 ml of water (deionized). Now, the filtered reaction mixture and subsequently two portions each of 300 ml, thus a total of 600 ml, of methylene chloride are passed in sequence and in each case with vigorous shaking through the four separating funnels $S_1$–$S_4$. The organic phases are combined, dried over 150 g of sodium sufate, filtered and evaporated up to constant weight in the rotary evaporator at the water-jet vacuum at a bath temperature of 50° C. There are obtained 46.9 g of crude product in the form of a yellow oil which, after purification on a chromatography column (silica gel; ether/n-hexane), gives 37.1 g of 3-(5-hydroxy-3-methyl-1,3-pentadienyl)-2,4,4-trimethyl-2-cyclohexan-1-one.

10 g of the thus-obtained substance are placed in 65 ml of methylene chloride in a 200 ml sulfonation flask, provided with stirrer, thermometer, 25 ml dropping funnel with pressure balance and an apparatus for inert gasification; thereupon the reaction vessel is flushed with argon and held under slight argon pressure during the entire reaction duration. Thereafter, the solution is cooled to 0° to 5° C. with an ice-bath and subsequently the reaction mixture is held in this temperature range up to the working-up.

As rapidly as the observance of this reaction temperature permits, 13.0 ml of hydrogen bromide solution (63% in water) are added dropwise with intensive stirring (in about 16 minutes). The reaction mixture is then stirred for a further 20 minutes.

Meanwhile, a 250 ml separating funnel ($S_1$) is charged with 110 ml of 10 percent sodium chloride and two further 250 ml separating funnels ($S_2+S_3$) are each charged with 110 ml, thus with a total of 220 ml, of 5 percent sodium bicarbonate solution.

For the working-up, the reaction mixture and subsequently 45 ml of methylene chloride are now passed in sequence and with in each case shaking through the three extraction vessels $S_1$–$S_3$. The two methylene chloride phases are combined, treated with 0.4 ml of 1,2-butylene oxide, dried with 20 g of sodium sulfate, filtered, rinsed with 250 ml of ethyl acetate and the filtrate is concentrated to a volume of about 50 ml in the rotary evaporator at the water-jet vacuum at a bath temperature of 30° C. The partial vacuum in the rotary evaporator is relieved with nitrogen, the concentrate is treated with 250 ml of ethyl acetate and, as described, again concentrated to a volume of 100 ml, gassed with nitrogen and then the thus-obtained solution of 3-(5-bromo-3-methyl-1-cis,3-trans-pentadienyl)-2,4,4-trimethyl-2-cyclohexen-1-one is further used directly for the preparation of the phosphonium salt.

A solution of 13.0 g of triphenylphosphine and 0.4 ml of 1,2-butylene oxide in 130 ml of ethyl acetate is placed in a 350 ml sulfonation flask, provided with stirrer, thermometer, 100 ml dropping funnel with pressure balance and an apparatus for inert gasification. The reaction vessel is gassed with argon during the entire reaction duration.

The solution of the 3-(5-bromo-3-methyl-1-cis, 3-trans-pentadienyl)-2,4,4-trimethyl-2-cyclohexen-1-one obtained above is now added dropwise at room temperature while stirring in the course of 2 hours.

At the appearance of the first turbidity manifestations in the reaction mixture (after about 10 minutes), seed crystals are added. The light yellow phosphonium salt progressively crystallizes out therefrom, and the temperature of the reaction mixture rises slightly (up to about 26° C.). After completed addition of the bromide, the mixture is stilled stirred for a further 18 hours and then the product is filtered off under suction under nitrogen.

The yellowish crystallizate is washed under nitrogen on the suction filter 2 times with 60 ml of ethyl acetate each time and then dried up to constant weight at 50° C. in the drying oven at the water-jet vacuum. There are obtained 20.6 g of [all trans-3methyl-5-(2,6,6-trimethyl-3-oxo-1-cyclohexen-1-yl)-2,4-pentadienyl]-triphenyl-phosphonium bromide.

In a 350 ml sulfonation flask, provided with stirrer, 25 ml dropping funnel with pressure equalization tube and an apparatus for inert gasification, thermometer and a filled calcium chloride tube, 20.6 g of the phosphonium bromide obtained according to the above details and 2.8 g of 2,7-dimethyl-octa-triene-(2,4,6)-dial-(1,8) are dissolved in 105 ml of methylene chloride with stirring and argon gasification. The solution obtained is, with continued stirring, cooled to 0°–5° C. with an ice-bath and treated dropwise in this temperature in the course of 11 minutes with 10.0 ml of sodium methylate solution (containing 2.08 g of $NaOCH_3$).

One hour thereafter the cooling bath is removed and 0.4 ml of acetic acid are added dropwise to the reaction mixture.

Afterwards, the calcium chloride tube is replaced by a distillation head with descending Liebig condenser. While warming with an oil-bath (62° C.) 19 ml of methylene chloride are firstly distilled off. Thereafter, with continued distillation, 127 ml of methanol are added dropwise to the mass through the dropping funnel so that the volume of the canthaxanthin solution remain approximately constant. Thereby, the canthaxanthin gradually crystallizes out in crystals which have a metallic lustre. Simultaneously, the vapor temperatures rises slowly from initially 36° C. up to 63° C. (oilbath temperature: 100° C.; total distillate: 110 ml). The thus-obtained crystal suspension is treated, still hot, with 12.7 ml of water and subsequently stirred at room temperature for 17 hours.

The crystals are filtered off with argon gasification and washed on the filter 2 times with 40 ml of 83 percent methanol each time and pressed out well.

If desired, the thus-obtained crude canthaxanthin can still be subjected to an isomerization (e.g. by heating to about 90° C. for about 15 hours) and a purification, there being obtained a product with a melting point of 199°–203° C.(not corr.).

EXAMPLE 2

The 5-(2,6,6-trimethyl-3-oxo-cyclohexen-1-yl)-3-methyl-2-trans-penten-4-yn-1-ol used as the starting material in accordance with Example 1 can be obtained as follows:

16.8 g of 2-hydroxy-3,5,5-trimethyl-2-cyclohexene-1,4-dione, 100 ml of ethylene chloride and 100 ml of formic acid are introduced into a 500 ml sulfonation flask, provided with stirrer, cooling apparatus, thermometer, calcium chloride tube and an apparatus for working under inert gas. Thereupon, 26.2 g of zinc dust are added portionwise while stirring within 10 minutes. The temperature thereby rises from 15° C. to 28° C. Subsequently, the reaction mixture is warmed with an oil-bath to 75° C. and left at this temperature for 5 ½ hours. For the working-up, the reaction mixture is cooled to 15° C. and stirred for 10 minutes. Thereupon, the reaction mixture is filtered, the zinc dust residue is washed on the filter 2 times with 150 ml of methylene chloride each time and the organic phase is rinsed into a 1-liter separating funnel $S_1$ and charged with 200 ml of saturated sodium chloride solution. Two further separating funnels $S_2$ and $S_3$ are charged each with 200 ml saturated sodium chloride solution. Through the three separating funnels $S_1$–$S_3$ there are passed in sequence, in each case with good intermixing, 2 portions each of 300 ml of methylene chloride. The combined organic phases are dried over 150 g of sodium sulfate, filtered and evaporated up to constant weight in the rotary evaporator at the water-jet vacuum at a bath temperature of 50° C. There are obtained 15.5 g of light yellow, crystalline crude product which is dissolved in 45 ml of diisopropyl ether while warming to 65° C. After cooling to about 40° C., the mixture is left to stand at −20° C. for 18 hours. The separated white crystals are filtered off, washed on the filter 2 times with 20 ml of diisopropyl ether (cooled to −20° C.) each time and then dried up to constant weight in the vacuum drying over at 40° C. There are obtained 14.9 g of a product with a melting point of 113°–115° C. which represents a tautomeric mixture of 3-hydroxy-2,6,6-trimethyl-2-cyclohexen-1-one and 3-hydroxy-2,4,4-trimethyl-2-cyclohexen-1-one.

15.4 g of the thus-obtained tautomeric mixture in 150 ml of acetone are introduced, together with 18.0 g of potassium carbonate, into a 350 ml sulfonation flask, which is provided with stirrer, cooling apparatus, calcium chloride tube and an apparatus for working under inert gas. Thereupon, 18.5 g of diethyl sulfate are added dropwise at 20° C. while stirring within about 5 minutes. Subsequently, the reaction mixture is warmed on an oil-bath to 56° C. and left at this temperature for 18 hours. For the working-up, the reaction mixture is cooled to 15° C. and thereupon evaporated up to constant weight in the rotary evaporator at the water-jet vacuum at a bath temperature of 50° C. The yellow residue obtained is dissolved in 250 ml of water and 250 ml of methylene chloride. The thus-obtained two-phase mixture is rinsed into a 1-liter separating funnel $S_1$. Two further one liter separating funnels $S_2$ and $S_3$ are charged with 250 ml of water in each case. In sequence and with good intermixing, 2 portions each of 250 ml of methylene chloride are passed through the 3 separating funnels $S_1$–$S_3$. The combined organic phases are dried over 150 g of sodium sulfate, filtered and evaporated up to constant weight in the rotary evaporator at the water-jet vacuum at a bath temperature of 50° C. The thus-obtained crude product is purified by means of column chromatography (silica gel, elution agent n-hexane/ether), there being obtained 12.7 g of 3-ethoxy-2,6,6-trimethyl-2-cyclohexen-1-one. A solution of 18.85 g of acetone=methyl-3-methyl-2-penten-4-ynyl-acetal in 135 ml of tetrahydrofuran is introduced into a 500 ml sulfonation flask, provided with stirrer, thermometer, cooling apparatus, calcium chloride tube, dropping funnel with pressure balance and an apparatus for inert gasification. With strong stirring and gassing with argon the temperature in the reaction vessel is lowered to −15° C. with the aid of a cooling bath (−20° C.) and there are thereupon added dropwise in the course of 15 minutes 66.6 ml of a 1.5M butyl lithium solution (6.4 g of butyl lithium) so that the temperature of the reaction mixture does not exceed −7° C. Subsequently, with continued stirring and gassing with argon, a solution of 15.49 g of the 3-ethoxy-2,6,6-trimethyl-2-cyclohexen-1-one obtained according to the above details in 35 ml of tetrahydrofuran is added dropwise in the course of 5 minutes. After removal of the cooling bath, the light yellow, clear solution obtained is warmed up to +10° C., left to react for a total of 3 ½ hours at this temperature and then treated dropwise, with renewed cooling (−20° C.) in the mass with 75 ml of 3N aqueous sulfuric acid so that the temperature of the reaction mixture does not exceed 0° C. After removal of the cooling bath, the thus-obtained two-phase mixture is vigorously stirred at room temperature for 3 hours and then rinsed into a one liter separating funnel $S_1$. Two further one liter separating funnels $S_2$ and $S_3$ are each charged with 150 ml of ether and the aqueous phase from $S_1$ and subsequently 3 portions each of 100 ml of saturated sodium bicarbonate solution are passed in sequence and with in each case shaking through the 3 separating funnels. The aqueous phases are discarded, the organic phases are combined, dried with 100 g of sodium sulfate, filtered and concentrated up to constant weight in the rotary evaporator at the water-jet vacuum at a bath temperature of 40° C. There are obtained 24.0 g of a light yellow, crystalline crude product which is dissolved in 50 ml of diisopropyl ether while warming to 65° C. After cooling to 55° C., the solution obtained is cooled to room temperature within one hour and then left to stand at −20° C. for a further 16 hours. The lemon colored, needle-like crystals obtained are filtered off with argon gasification, washed on the filter 2 times with 20 ml of diisopropyl ether (cooled to −20° C.) each time and then dried up to constant weight in the vacuum drying oven at 40° C. There is thereby obtained 5-(2,6,6-trimethyl-3-oxo-cyclohexen-1-yl)-3-methyl-2-trans-penten-4-yn-1-ol with a melting point of 103.5° C.–105.5° C.

We claim:

1. A process comprising hydrogenating a compound of the formula:

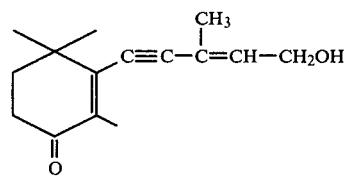

by treating said compound with zinc and a carboxylic acid having from 1 to 3 carbon atoms to produce a compound of the formula

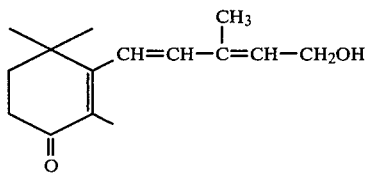

2. The process of claim 1 wherein said acid is acetic acid.

3. The process of claim 1 wherein said acid is propionic acid.

4. A process comprising hydrogenating a compound of the formula

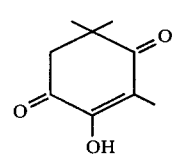

by treating said compound with zinc and a carboxylic acid having from 1 to 3 carbon atoms to form a compound of the formula:

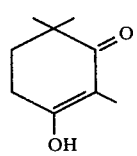

5. The process of claim 3 wherein said acid is formic acid.

* * * * *